(12) United States Patent
Lee et al.

(10) Patent No.: US 11,255,863 B2
(45) Date of Patent: Feb. 22, 2022

(54) METHOD FOR DETECTING AGGREGATE OF AGGREGATE-FORMING POLYPEPTIDE

(71) Applicant: PEOPLEBIO, INC., Gyeonggi-do (KR)

(72) Inventors: Byoung Sub Lee, Gyeonggi-do (KR); Kwan Soo Lee, Seoul (KR); Shin Won Kim, Seoul (KR); Kun Taek Lim, Gyeonggi-do (KR); Gwang Je Kim, Incheon (KR); Ji Sun Yu, Seoul (KR)

(73) Assignee: PEOPLEBIO, INC., Gyeonggi-do (KR)

( * ) Notice: Subject to any disclaimer, the term of this patent is extended or adjusted under 35 U.S.C. 154(b) by 165 days.

(21) Appl. No.: 16/085,070

(22) PCT Filed: Mar. 16, 2017

(86) PCT No.: PCT/KR2017/002858
§ 371 (c)(1),
(2) Date: Sep. 14, 2018

(87) PCT Pub. No.: WO2017/160104
PCT Pub. Date: Sep. 21, 2017

(65) Prior Publication Data
US 2019/0120859 A1   Apr. 25, 2019

(30) Foreign Application Priority Data
Mar. 16, 2016   (KR) .................. 10-2016-0031534

(51) Int. Cl.
*G01N 33/68* (2006.01)
*G01N 33/543* (2006.01)

(52) U.S. Cl.
CPC ... *G01N 33/6896* (2013.01); *G01N 33/54306* (2013.01); *G01N 2333/4709* (2013.01); *G01N 2800/2821* (2013.01)

(58) Field of Classification Search
CPC ......... G01N 33/6896; G01N 33/54306; G01N 2800/2821; G01N 2333/4709
See application file for complete search history.

(56) References Cited

U.S. PATENT DOCUMENTS

| | | | |
|---|---|---|---|
| 8,008,026 B2 | 8/2011 | An et al. | |
| 8,026,070 B2 | 9/2011 | An et al. | |
| 9,625,459 B2 | 4/2017 | Staffler et al. | |
| 2010/0009388 A1* | 1/2010 | An | G01N 33/6896 435/7.9 |
| 2010/0069494 A1* | 3/2010 | Zawia | A61P 25/28 514/567 |
| 2012/0009595 A1* | 1/2012 | Lane | G01N 33/54326 435/7.5 |
| 2012/0190672 A1* | 7/2012 | Hall | A61P 25/28 514/224.2 |
| 2013/0109581 A1* | 5/2013 | Salisbury | G01N 33/531 506/9 |
| 2013/0149700 A1 | 6/2013 | Weber et al. | |
| 2014/0370620 A1 | 12/2014 | Chung et al. | |
| 2015/0276771 A1 | 10/2015 | Madasamy | |
| 2017/0261521 A1 | 9/2017 | Lee et al. | |

FOREIGN PATENT DOCUMENTS

| | | |
|---|---|---|
| CN | 101124342 A | 2/2008 |
| CN | 101308144 A | 11/2008 |
| JP | 2008530578 A | 8/2008 |
| JP | 2009534648 A | 9/2009 |
| JP | 2014529087 A | 10/2014 |
| JP | 2015-500502 A | 1/2015 |
| JP | 2015-500502 A5 | 1/2015 |
| KR | 10-2011-0081330 A | 7/2011 |
| KR | 10-1352849 B1 | 1/2014 |
| KR | 10-2014-0069346 A | 6/2014 |
| KR | 10-2015-0008309 A | 1/2015 |
| KR | 10-2016-0067026 A | 6/2016 |
| WO | WO-2012-149365 A2 | 11/2012 |
| WO | WO-2013-081946 A1 | 6/2013 |
| WO | WO-2012-149365 A3 | 2/2014 |

OTHER PUBLICATIONS

Office Action from corresponding Korean Patent Application No. 10-2019-0037110, dated Jun. 5, 2019.
Anaspec, 'Alzheimer's Research_World's largest collection of β-Amyloid peptides', 2nd edition, 2010, pp. 1-24.
D. C. Crowther et al., 'Anassay for Seeded Proteinaggregation Detects Abeta Seeds in Serum', Oral Sessions: O4-10: Biomarkers: Blood-Based Abeta and Tau Markers, 2014.
Pitschke M. et al., 'Detection of single amyloid beta-protein aggregates in the cerebrospinal fluid of Alzheimer's patients by fluorescence correlation spectroscopy', nat Med, 1998, vol. 4, and the pp. 832-834.
Ruiz et al., "Blood Amyloid Beta Levels in Healthy, Mild Cognitive Impairment and Alzheimer's Disease Individuals: Replication of Diastolic Blood Pressure Correlations and Analysis of Critical Covariates" PLOS ONE, 2013, vol. 8, Issue 11, e81334.
International Search Report (ISR) from corresponding PCT Application No. PCT/KR2017/002858, dated Jul. 17, 2017, and its English translation.

(Continued)

*Primary Examiner* — Changhwa J Cheu
(74) *Attorney, Agent, or Firm* — Harness, Dickey & Pierce, P.L.C.

(57) ABSTRACT

The present invention relates to a method for detecting an aggregate of an aggregate-forming polypeptide of a biosample, comprising (a) a step of spiking a dimer type of the aggregate-forming polypeptide into the biosample to be analyzed; (b) a step of incubating a resultant product of step (a) to further form an aggregate of the aggregate-forming polypeptide; (c) a step of contacting a resultant product of step (b) with a binding agent-tag in which a signal-generating tag is bound to a binding agent that binds to the aggregate of the aggregate-forming polypeptide; and (d) a step of detecting a signal which is generated from the binding agent-tag bound to the aggregate of the aggregate-forming polypeptide.

13 Claims, 7 Drawing Sheets
Specification includes a Sequence Listing.

(56) References Cited

OTHER PUBLICATIONS

An, et al. (2017) "Dynamic changes of oligomeric amyloid β levels in plasma induced by spiked synthetic Aβ42." *Alzheimer's Research & Therapy*, 9:86, pp. 1-10.

Conway, et al. (1998) "Accelerated in vitro fibril formation by a mutant α-synuclein linked to early-onset Parkinson disease." *Nature Medicine*, 4(11):1318-1320.

Wolozin, B., MD, PhD. and Behl, C., PhD. (2000) "Mechanisms of Neurodegenerative Disorders." *Arch Neurol.* vol. 57, pp. 793-796. (Downloaded from: http://archneur.jamanetwork.com/ on <http://archneur.jamanetwork.com/on> Jan. 21, 2013).

Japanese Office Action dated Sep. 14, 2018 issued in Japanese Patent Application No. JP 2018-548776, with English Translation.

Supplementary Partial European Search Report, dated Aug. 22, 2019 in European Patent Application No. 17767005.6.

Decision to Grant a Patent of Japanese Patent Application No. 2018-548776 dated Jul. 21, 2020, with English translation.

* cited by examiner

METHOD FOR DETECTING AGGREGATE OF AGGREGATE-FORMING POLYPEPTIDE

CROSS-REFERENCE TO RELATED APPLICATIONS

This application is a national phase application of PCT Application No. PCT/KR2017/002858, filed on Mar. 16, 2017, which claims the benefit and priority to Korean Patent Application No. 10-2016-0031534, filed Mar. 16, 2016. The entire disclosures of the applications identified in this paragraph are incorporated herein by references.

TECHNICAL FIELD

Background

First, in some cases, polypeptides constituting proteins make functional proteins by forming multimers. However, when polypeptides present as monomers in a normal state form multimers, they aggregate abnormally (e.g., being converted into a misfolded form), and cause diseases (Massimo Stefani, et al., *J. Mol. Med.* 81:678-699(2003); and Radford S E, et al., *Cell.* 97:291-298(1999)).

For example, the diseases or disorders associated with abnormal aggregation or misfolding of proteins include Alzheimer's disease, Creutzfeldt-Jakob disease, spongiform encephalopathies, Parkinson's disease, Huntington's disease, amyotrophic lateral sclerosis, Serpin deficiency, emphysema, cirrhosis, type II diabetes, primary systemic amyloidosis, secondary systemic amyloidosis, frontotemporal dementias, senile systemic amyloidosis, familial amyloid polyneuropathy, hereditary cerebral amyloid angiopathy, and haemodialysis-related amyloidosis.

In measuring the presence or absence or the progress of such diseases or disorders, when such measurement is difficult since the amount of the antigen is very small in the sample or the size of the antigen is very small, or when the amount of the antigen in the body is not proportional to the amount of the antigen in the sample, for example, (although the level of Aβ (amyloid-beta), which is implicated in Alzheimer's disease, is known to be higher in an abnormal person than in a normal person), when the amount of the Aβ oligomer in a blood sample is difficult to detect or the Aβ oligomer exits atypically in the blood sample, diagnosis may be difficult.

In addition, the antigen to be measured is too small in size or too small in amount, and thus, the diagnosis of diseases is often not easy by sandwich ELISA.

Accordingly, the present inventors recognized a need for the development of a method for detecting an aggregate form of an aggregate-forming polypeptide, the method maximizing the difference in diagnostic signal between a patient and a normal subject.

DETAILED DESCRIPTION

Technical Problem

Under the above background, the present inventors have conducted extensive research to develop a novel method for detecting an aggregate form of an aggregate-forming polypeptide, and as a result the present inventors have developed a method for detecting an aggregate form of an aggregate-forming polypeptide, the method maximizing a difference in diagnostic signal between a patient and a normal subject using a difference in the clearing system suppressing the formation of an aggregate form of a polypeptide.

Therefore, an aspect of the present invention is to provide a method for detecting an aggregate form of an aggregate-forming polypeptide in a biosample.

Another aspect of the present invention is to provide a kit for detecting an aggregate form of an aggregate-forming polypeptide in a biosample.

Technical Solution

In accordance with an aspect of the present invention, there is provided a method for detecting an aggregate form of an aggregate-forming polypeptide in a biosample, the method including the steps of: (a) spiking a dimeric form of the aggregate-forming polypeptide with a biosample to be analyzed; (b) additionally forming an aggregate form of the aggregate-forming polypeptide by incubating a product of step (a); (c) contacting, with a product of step (b), a binder-label in which a signal generation label is conjugated to a binder binding to the aggregate form of the aggregate-forming polypeptide; and (d) detecting a signal generated from the binder-label, which is bound to the aggregate form of the aggregate-forming polypeptide, wherein the incubating in step (b) is carried out for a sufficient incubation time for multimerization of the spiked dimeric form of the aggregate-forming polypeptide by the biosample.

The present invention is directed to a method for detecting an aggregate form of an aggregate-forming polypeptide, the method maximizing the difference in diagnostic signal between a patient and a normal subject using a difference in the clearing system suppressing the formation of an aggregate form of a polypeptide.

As used herein, the term "aggregate-forming polypeptide" refers to a polypeptide capable of forming a multimeric form (oligomeric form) or forming an aggregate form through hydrophobic interaction with monomers. In particular, the structural changes above cause various diseases. Examples thereof include Alzheimer's disease, Creutzfeldt-Jakob disease, spongiform encephalopathies, Parkinson's disease, Huntington's disease, amyotrophic lateral sclerosis, Serpin deficiency, emphysema, cirrhosis, type II diabetes, primary systemic amyloidosis, secondary systemic amyloidosis, frontotemporal dementias, senile systemic amyloidosis, familial amyloid polyneuropathy, hereditary cerebral amyloid angiopathy, and haemodialysis-related amyloidosis.

Generally, a non-aggregate form of the aggregate-forming polypeptide is normal, but an aggregate form thereof causes, especially, a neurodegenerative disease, such as, Alzheimer's disease, Creutzfeldt-Jakob disease, or Parkinson's disease.

According to an embodiment of the present invention, the biosample for performing the multimerization of the spiked dimeric form of the aggregate-forming polypeptide is a biosample from a human being having a disease associated with the multimeric form of the aggregate-forming polypeptide. More preferably, the sufficient incubation time to perform multimerization by the biosample refers to a time sufficient to enhance a signal generated using the biosample from the human being having a disease associated with the multimeric form of the aggregate-forming polypeptide to be 1.3-20 times greater than a signal generated using a biosample from a normal human being.

Hereinafter, the method of the present invention for detecting an aggregate form of an aggregate-forming polypeptide in a biosample will be described in detail step by step.

(a) Step of Performing Spiking

First, the method of the present invention includes a step of spiking a dimeric form of the aggregate-forming polypeptide with a biosample to be analyzed.

As used herein, the term "biosample" refers to an organism-originated sample to be analyzed. The biosample refers to any cell, tissue, or biofluid from a biological source, or any other medium that can be analyzed according to the present invention, and the biosample includes a sample collected from a human being, a sample collected from an animal, and a sample collected from a food for a human being or animal. Preferably, the biosample to be analyzed is a body fluid sample including blood, serum, plasma, lymph, milk, urine, feces, ocular fluid, saliva, semen, brain extracts (e.g., brain homogenates), spinal cord fluid (SCF), appendix, spleen, and tonsillar tissue extracts. More preferably, the biosample is blood, most preferably plasma.

According to another embodiment of the present invention, the aggregate-forming polypeptide includes Aβ peptide and tau protein involved in Alzheimer's disease, prion involved in Creutzfeldt-Jakob disease and sponge foam brain disease, α-synuclein involved in Parkinson's disease, in Ig light chain involved in primary systemic amyloidosis, serum amyloid A involved in secondary systemic amyloidosis, tau protein involved in frontotemporal dementias, transthyretin involved in senile systemic amyloidosis, transthyretin involved in familial amyloid multiple neuropathy, cystatin C involved in hereditary cerebral amyloid angiopathy, β2-microglobulin involved in haemodialysis-related amyloidosis, Huntingtin involved in Huntington's disease, superoxide dismutase involved in amyotrophic lateral sclerosis, serpin involved in serpin deficiency, pulmonary emphysema, and cirrhosis, and amylin involved in type II diabetes. More preferably, the aggregate-forming polypeptide is Aβ peptide or tau protein involved in Alzheimer's disease, or α-synuclein involved in Parkinson's disease, most preferably, Aβ peptide.

As used herein, the term "spiking" refers to an addition of a dimeric form of an aggregate-forming polypeptide to a biosample to be analyzed or a mixing after addition thereof.

As used herein, the term "multimer" also includes an oligomer.

As used herein, the term "dimer" refers to one formed by combining two monomers.

According to the present invention, in case where a dimeric form of the aggregate-forming polypeptide is spiked with a biosample to be analyzed, the difference in the diagnostic signal between a patient and a normal subject is intended to be maximized using a difference in the clearing system suppressing the formation of an aggregate form of an aggregate-forming polypeptide, that is, a biosample of the patient has a low degree of the clearing system, promoting the formation of an aggregate form of an aggregate-forming polypeptide, but a biosample of a normal subject has a high degree of the clearing system, reducing the formation of an aggregate form of a aggregate-forming polypeptide, thereby maximizing the difference in diagnostic signal.

According to still another embodiment of the present invention, the dimeric form of the aggregate-forming polypeptide is formed by disulfide bonding of two Aβ peptides each composed of the amino acid sequence of SEQ ID NO: 1, which is a monomeric form of the aggregate-forming polypeptide, by means of the 26$^{th}$ Cys residues of the Aβ peptides each composed of the amino acid sequence of SEQ ID NO: 1.

According to another embodiment of the present invention, a buffer is additionally added to the product in step (a).

More preferably, the buffer is added in an amount of 3-15 times (v/v) to a biosample, still more preferably, 5-13 times (v/v), yet more preferably, 7-11 times (v/v), and even more preferably 8-10 times (v/v).

For the buffer used in the present invention, various buffers known in the art may be used, but preferably, the buffer is a non-ionic surfactant-containing phosphate buffer.

For the non-ionic surfactant contained in the phosphate buffer used in the present invention, various non-ionic surfactants known in the art may be used, and preferably the non-ionic surfactant includes alkoxylated alkyl ethers, alkoxylated alkyl esters, alkyl polyglycosides, polyglyceryl esters, polysorbates, and sugar esters. More preferably, Tween-20 or Triton X-100 is used, and most preferably, Tween-20 is used.

(b) Step of Additionally Forming Aggregate Form of Aggregate-Forming Polypeptide Then, the method of the present invention includes (b) step of additionally forming an aggregate form of the aggregate-forming polypeptide by incubating the product of step (a).

One of the features of the present invention is that in cases where a measurement is difficult to make due to a very small amount of an aggregate form of aggregate-forming polypeptide (antigen), which is to be measured, in a sample or a very small size of an aggregate form of aggregate-forming polypeptide or when the amount of an aggregate form of aggregate-forming polypeptide (antigen) in the body is not proportional to the amount of an aggregate form of aggregate-forming polypeptide (antigen) in the sample, the presence or absence or the progress of diseases or disorders can be measured by spiking the dimeric form of aggregate-forming polypeptide with the biosample to additionally form an aggregate form of aggregate-forming polypeptide.

According to another embodiment of the present invention, the additional forming of the aggregate form of the aggregate-forming polypeptide in step (b) is conducted by incubating the product in step (a) at a temperature of 1-50° C., more preferably 35-50° C., still more preferably 35-45° C., still more preferably 35-40° C.

In the present invention, the incubating in step (b) is conducted for a sufficient time for multimerization of the spiked dimeric form of aggregate-forming polypeptide by the biosample. More preferably, the sufficient incubation time for multimerization by the biosample is a time sufficient to enhance a signal generated using the biosample from the human being having a disease associated with the multimeric form of the aggregate-forming polypeptide to be 1.3-20 times greater than a signal generated using a biosample from a normal human being.

According to still another embodiment of the present invention, the additional forming of the aggregate form of the aggregate-forming polypeptide in step (b), in order to conduct for a time sufficient to enhance a signal generated using the biosample from a human being to be 1.3-20 times greater than a signal generated using a biosample from a normal human being, is conducted by incubating the product in step (a) for 1 to 12 days, preferably for 1 to 10 days, more preferably for 1 to 8 days, still more preferably for 1 to 6 days, still more preferably for 1 to 6 days, still more preferably for 2 to 6 days, and most preferably for 2 to 5 days.

As used herein, the term "incubation" refers to standing (kept to stand) or shaking a biosample to be analyzed at a predetermined temperature for a predetermined period of time, and the shaking is, preferably, mild shaking.

Another of the greatest features of the present invention is that a biosample is allowed to stand (i.e., incubation) at a predetermined temperature for a predetermined period of time, so that a dimeric form of the aggregate-forming polypeptide and the aggregate-forming polypeptide, which exist in the biosample, aggregate well together, thereby maximizing the difference in diagnostic signal between a patient and a normal subject.

(c) Step of Contacting, With Product in Step (b), Binder-Label Binding to Aggregate Form of Aggregate-Forming Polypeptide Then, the method of the present invention includes step (c) of contacting, with a production of step (b), a binder-label in which a signal generating label is conjugated to a binder binding to the aggregate form of the aggregate-forming polypeptide.

In the present invention, the binder binding to the aggregate form of the aggregate-forming polypeptide includes an antibody, a peptide aptamer, an adnectin, an affibody (U.S. Pat. No. 5,831,012), an avimer (Silverman, J. et al, *Nature Biotechnology* 23(12):1556(2005)) or a Kunitz domain (Arnoux B et al., *Acta Crystallogr. D Biol. Crystallogr.* 58(Pt 7):12524(2002), and Nixon, A E, *Current opinion in drug discovery & development* 9(2):2618(2006)).

In the present invention, the signal generation label, which is conjugated to the binder binding to the aggregate form of the aggregate-forming polypeptide, includes a compound label (e.g., biotin), an enzyme label (e.g., alkaline phosphatase, peroxidase, β-galactosidase, and β-glucosidase), a radioactive label (e.g., $I^{125}$ and $C^{14}$), a fluorescent label (e.g., fluorescein), a luminescent label, a chemiluminescent label, and a fluorescence resonance energy transfer (FRET) label, but is not limited thereto.

(d) Step of Detecting Signal Generated From Binder-Label Bound to Aaggregate Form of Aggregate-Forming Polypeptide Last, the method of the present invention includes step (d) of detecting a signal generated from the binder-label bound to the aggregate form of the aggregate-form ing polypeptide.

The detecting of the signal generated from the binder-label bound to the aggregate form of the aggregate-forming polypeptide may be conducted by various methods known in the art, and for example, an immunoassay method associated with an antigen-antibody response may be used.

According to still another embodiment of the present invention, steps (c) and (d) are performed by a method including the following steps: (c-1) contacting the product of step (b) with a capture antibody recognizing an epitope on the aggregate-form ing polypeptide capturing the aggregate form; (c-2) contacting the captured aggregate form with a detection antibody recognizing an epitope on the aggregate-form ing polypeptide; and (c-3) detecting an aggregate form-detection antibody complex.

Such a detection method employs two types of antibodies, namely, a capture antibody and a detection antibody. As used herein, the term "capture antibody" refers to an antibody that can bind to an aggregate-forming polypeptide to be detected in a biosample. The term "detection antibody" refers to an antibody that can bind to an aggregate-forming polypeptide captured by the capture antibody. The term "antibody" refers to an immunoglobulin protein that can bind to an antigen. The antibody used herein includes antibody fragments (e.g., F(ab')2, Fab', Fab, Fv) as well as a whole antibody that can bind to an epitope, an antigen, or an antigen fragment.

The detection method employs one set of a capture antibody and a detection antibody, which specifically recognize epitopes on an aggregate-forming polypeptide, and the epitopes specifically recognized by the capture antibody and the detection antibody are identical to or are overlapped with each other.

As used herein to recite the epitopes with respect to the capture antibody and the detection antibody, the term "overlapped with" encompasses epitopes having completely or partially overlapped with amino acid sequences. For example, epitopes to 6E10, FF51, and WO2 antibodies have the amino acid sequences including amino acids 3-8, 1-4, and 4-10, respectively, of the human Aβ peptide sequence. Such epitopes may be explained as completely overlapped epitopes.

According to another embodiment of the present invention, the epitopes, when expressed to recite the human Aβ peptide sequence, have the amino acid sequence of amino acids 3-8, 1-4, or 4-10.

According to still another embodiment of the present invention, the epitope recognized by the capture antibody has a sequence that is not repeated in the aggregate-forming polypeptide, and the epitope recognized by the detection antibody has a sequence that is not repeated in the aggregate-forming polypeptide. According to the detection method of the present invention, the aggregate-forming polypeptide bound to the capture antibody cannot bind to the detection antibody any more, and the reason is that there is no additional epitope recognized by the detection antibody.

According to another embodiment of the present invention, the capture antibody and the detection antibody are identical to each other. That is, the epitopes, specifically bound to the capture antibody and the detection antibody, are preferably identical to each other.

According to still another embodiment of the present invention, the capture antibody binds to a solid substrate. Such a known material includes polystyrene, polypropylene, glass, metal, and a hydrocarbon polymer, such as a gel. The solid substrate may be present in the form of a dipstick, a microtiter plate, particle (e.g., bead), an affinity column, and an immunoblot membrane (e.g., a polyvinylidene fluoride membrane) (see, U.S. Pat. Nos. 5,143,825, 5,374,530, 4,908, 305, and 5,498,551).

According to another embodiment of the present invention, the detection antibody has a label generating a detectable signal. The label includes a compound label (e.g., biotin), an enzyme label (e.g., alkaline phosphatase, peroxidase, β-galactosidase, and β-glucosidase), a radioactive label (e.g., $I^{125}$ and $C^{14}$), a fluorescent label (e.g., fluorescein), a luminescent label, a chemiluminescent label, and a fluorescence resonance energy transfer (FRET) label, but is not limited thereto. Various labels and methods for labeling antibodies are known in the art (Harlow and Lane, eds. *Antibodies: A Laboratory Manual* (1988) Cold Spring Harbor Laboratory Press, Cold Spring Harbor, N.Y.).

In the present invention, the antibodies that can be bound to the aggregate-forming polypeptide may be prepared using epitopes previously described as immunogens according to the prior art, such as a fusion method (Kohler and Milstein, *European Journal of Immunology*, 6:511-519(1976)), a recombinant DNA method (U.S. Pat. No. 4,816,567), or a phage antibody library method (Clackson et al, *Nature*, 352:624-628(1991) and Marks et al, *J. Mol. Biol.*, 222:58, 1-597(1991)). General methods for preparing the antibodies are described in Harlow, E. and Lane, D., *Antibodies: A Laboratory Manual*, Cold Spring Harbor Press, New York, 1988; Zola, H., Monoclonal Antibodies: *A Manual of Techniques*, CRC Press, Inc., Boca Raton, Fla., 1984; and Coligan, CURRENT PROTOCOLS IN IMMUNOLOGY, Wiley/Greene, N.Y., 1991.

The preparation of hybridoma cell lines for the production of monoclonal antibodies is conducted by the fusion of an immortal cell line and antibody-producing lymphocytes. The preparation of monoclonal antibodies may be conducted using techniques known in the art. The polyclonal antibodies may be prepared by injecting the foregoing antigen into a suitable animal, collecting anti-serum containing an antibody, and then isolating the antibody by a method for isolating an antibody through a known affinity technique.

The detection of the aggregate form-detection antibody complex may be conducted by various methods known in the art. The formation of the aggregate form-detection antibody complex shows the presence of the aggregate form in the biosample. The step above may be quantitatively or qualitatively conducted using various detectable label/substrate pairs disclosed in, for example, *Enzyme Immunoassay*, E. T. Maggio, ed., CRC Press, Boca Raton, Fla., 1980 and Harlow and Lane, eds. *Antibodies: A Laboratory Manual* (1988) Cold Spring Harbor Laboratory Press, Cold Spring Harbor, N.Y., by the conventional methods.

In cases where the detection antibody is labeled with alkaline phosphatase, bromochloroindolylphosphate (BCIP), nitro blue tetrazolium (NBT), or ECF may be used as a substrate for a color development reaction; in cases where the detection antibody is labeled with horseradish peroxidase, chloronaphthol, aminoethyl carbazole, diaminobenzidine, D-luciferin, lucigenin (bis-N-methylacridinium nitrate), resorufin benzyl ether, luminol, Amplex Red reagent (10-acetyl-3,7-dihydroxyphenoxazine), TMB (3,3,5,5-tetramethylbenzidine), enhanced chemiluminescence (ECL), or ABTS (2,2-azine-di[3-ethylbenzthiazoline sulfonate]) may be used as a substrate.

Through such methods, the signal generated using a biosample from a human being having a disease associated with a multimeric form of an aggregate-forming polypeptide can be enhanced compared with the signal generated using a biosample from a normal human being by 1.3-20 times, preferably by 1.5-10 times, and more preferably by 1.6-10 times.

In accordance with another aspect of the present invention, there is provided a kit for detecting an aggregate form of an aggregate-forming polypeptide in a biosample containing a dimeric form of an aggregate-forming polypeptide.

The kit of the present invention uses the foregoing method for detecting an aggregate form of an aggregate-forming polypeptide in a biosample of the present invention, and thus the description of overlapping contents therebetween will be omitted to avoid excessive complexity of the specification due to repetitive descriptions thereof.

According to another embodiment of the present invention, the kit further comprises: a capture antibody recognizing an epitope on the aggregate-forming polypeptide; and a detection antibody recognizing the epitope recognized by the capture antibody.

Advantageous Effects

Features and advantages of the present invention are summarized as follows.

(a) The present invention provides a method or kit for detecting an aggregate form of an aggregate-forming polypeptide in a biosample.

(b) In the method of the present invention, in cases where a measurement is difficult to make due to a very small amount of an aggregate form of aggregate-forming polypeptide (antigen), which is to be measured, in a sample or a very small size of an aggregate form of aggregate-forming polypeptide or when the amount of an aggregate form of aggregate-forming polypeptide (antigen) in the body is not proportional to the amount of an aggregate form of aggregate-forming polypeptide (antigen) in the sample, the difference in diagnostic signal between a patient and a normal subject is maximized by using the difference in the clearing system that suppresses the formation of an aggregate form of a polypeptide.

(c) The present invention can be carried out in a convenient and prompt manner, and can automate a method for detecting an aggregate form of an aggregate-forming polypeptide in a biosample.

MODE FOR CARRYING OUT THE INVENTION

Figure 1:
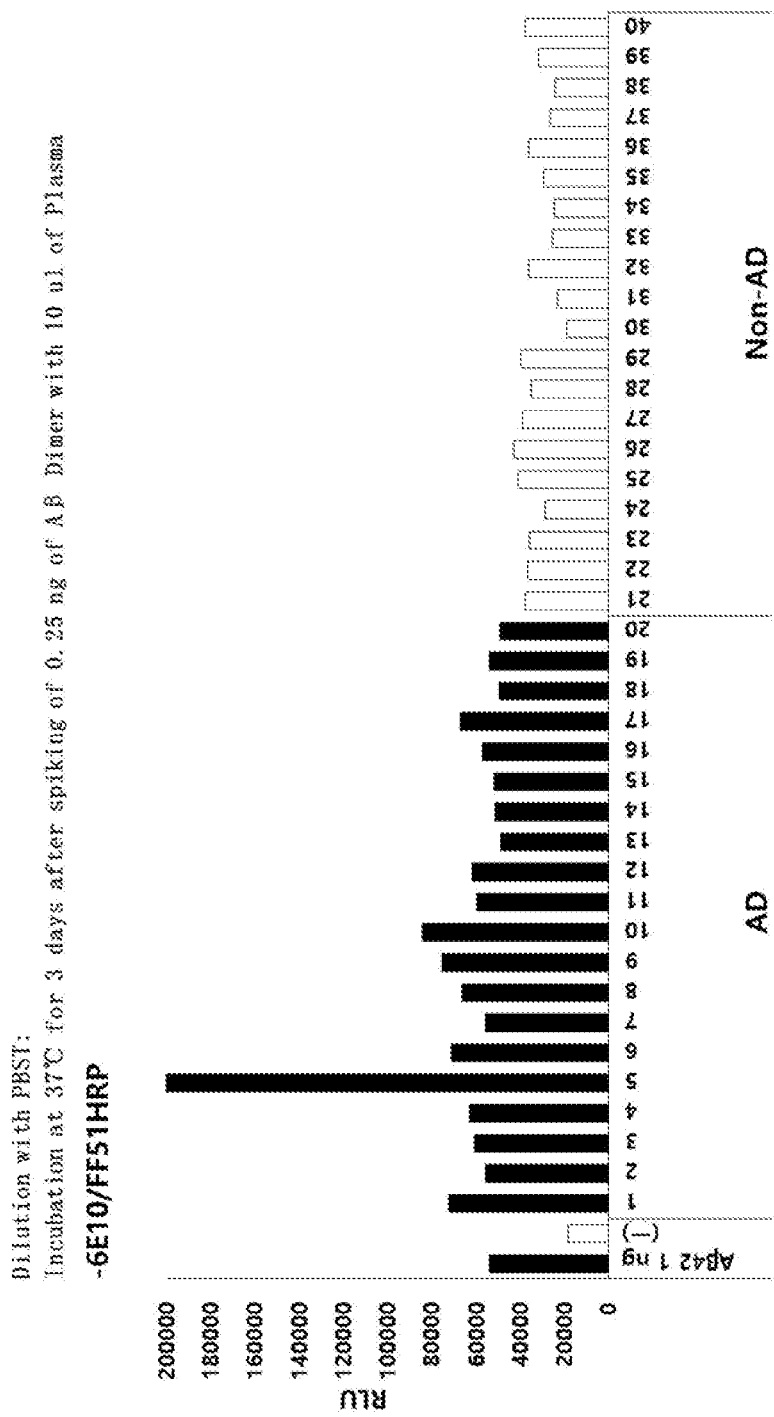
FIGS. 1 and 2 show the detection results of Aβ oligomer using multimer detection system (MDS) (6E10/FF51HRP set) from samples incubated for 3 and 4 days after treatment with S26C-Beta-Amyloid (1-40) Dimer according to examples of the present invention.

Hereinafter, the present invention will be described in detail with reference to examples. These examples are only for illustrating the present invention more specifically, and it will be apparent to those skilled in the art that the scope of the present invention is not limited by these examples.

EXAMPLES

Example 1

Materials

A coating buffer (Carbonate-Bicarbonate Buffer), PBST, TBST, and PBS were purchased from Sigma. Block Ace was purchased from Bio-rad. Buffer A was prepared by diluting Block Ace to 0.4% in TBST. A blocking buffer was prepared by diluting 1% Block Ace to 0.4% in TBST. HBR1 was purchased from Scantibodies Laboratory. 6E10 antibody was purchased from Biolegend. WO2-HRP antibody was purchased from Absolute Antibody. FF51-HRP was purchased from The H lab. WO2-HRP antibody was purchased from Absolute Antibody. Recombinant Aβ1-42 was purchased from Biolegend. Recombinant S26C-Beta-Amyloid (1-40) Dimer was purchased from JPT. Plasma samples were obtained from Seoul National University Bundang Hospital and Chungang University Hospital. ECL solution was purchased from Rockland. Plates were purchased from Nunc. Epitopes to 6E10, FF51, and WO2 antibodies have the amino acid sequences including amino acids 3-8, 1-4, and 4-10, respectively, of the human Aβ peptide sequence. The sequence of S26C-Beta-Amyloid (1-40) dimer is DAE-FRHDSGYEVHHQKLVFFAEDVGCNK-GAIIGLMVGGVV, and has a dimeric form from a disulfide bond of the $26^{th}$ cysteine residues of respective monomers.

Example 2

Preparation of 6E10 Plate

After 30 μg of 6E10 antibody (anti-Aβ protein, Biolegend) was diluted in 10 ml of a coating buffer (Sigma), 100 μl was dispensed into each well in a plate (Nunc), followed by reaction in a refrigerator at 4° C. for one day. The plate was washed three times with PBS, and 240 μl of a blocking buffer in which 1% Block Ace was dissolved in D. W. was dispensed, followed by reaction at room temperature for 2 hours or more. The plate was washed with three times with BPS, and was then dried at room temperature for 30 minutes before.

Example 3

Preparation of Control

For a positive control, 990 μl of PBST was added to 10 μl of recombinant Aβ1-42(rec. Aβ) (1 μg/ml), and 100 μl of the resulting product was used. For a negative control, 100 μl of PBS was used.

Example 4

Preparation of Samples

Sample preparation was made based on two types of samples. Frozen plasma samples were dissolved in a 37° C. heat block for 15 minutes, followed by vortexing for 30 seconds before use. For samples spiked with 0.25 ng of S26C-Beta-Amyloid (1-40) Dimer, 8.08 μl of HBR1 (0.123 mg/ml), 180 μl of PBST, and 20 μl of S26C-Beta-Amyloid (1-40) Dimer(0.25 ng/10 μl) were mixed with 20 μl of plasma to prepare a total of 228.08 μl. For samples spiked with a recombinant peptide, 8.08 μl of HBR1 (0.123 mg/ml) and 200 μl of PBST were mixed with 20 μl of plasma to prepare a total of 228.08 μl.

Example 5

Incubation

The samples prepared by the treatment with S26C-Beta-Amyloid (1-40) Dimer in example 4 were incubated in a 37° C. incubator for 0, 1, 2, 3, 4, and 5 days, respectively (6E10/FF51HRP set). The samples prepared by the treatment without S26C-Beta-Amyloid (1-40) Dimer in example 4 were incubated in a 37° C. incubator for 0 and 5 days, respectively (6E10/FF51HRP set). In addition, the samples prepared by the treatment with S26C-Beta-Amyloid (1-40) Dimer in example 4 were incubated in a 37° C. incubator for 0, 1, 2, 3, 4, and 5 days, respectively (6E10/WO2HRP set).

Example 6

6E10/FF51HRP Set

Detection of Aβ oligomer using multimer detection system (MDS) from samples incubated for 3 and 4 days after treatment with S26C-Beta-Amyloid (1-40) Dimer The positive control, the negative control, and the samples treated with 0.25 ng of S26C-Beta-Amyloid (1-40) Dimer and incubated for 3 and 4 days were dispensed in 100 μl each on 6E10 coated plate (3 μg/ml), followed by reaction at room temperature for 1 hour. The plate was washed three times with TBST. FF51-HRP antibody was added to buffer A to reach 0.5 μg/ml, and then 100 μl each was dispensed. The plate was washed three times with TBST, and 100 μl of the ECL solution was dispensed. The plate reacted with ELC was inserted into a luminometer (PerkinElmer) to measure a luminescent signal. The results are shown in FIGS. 1 and 2.

Figure 2:
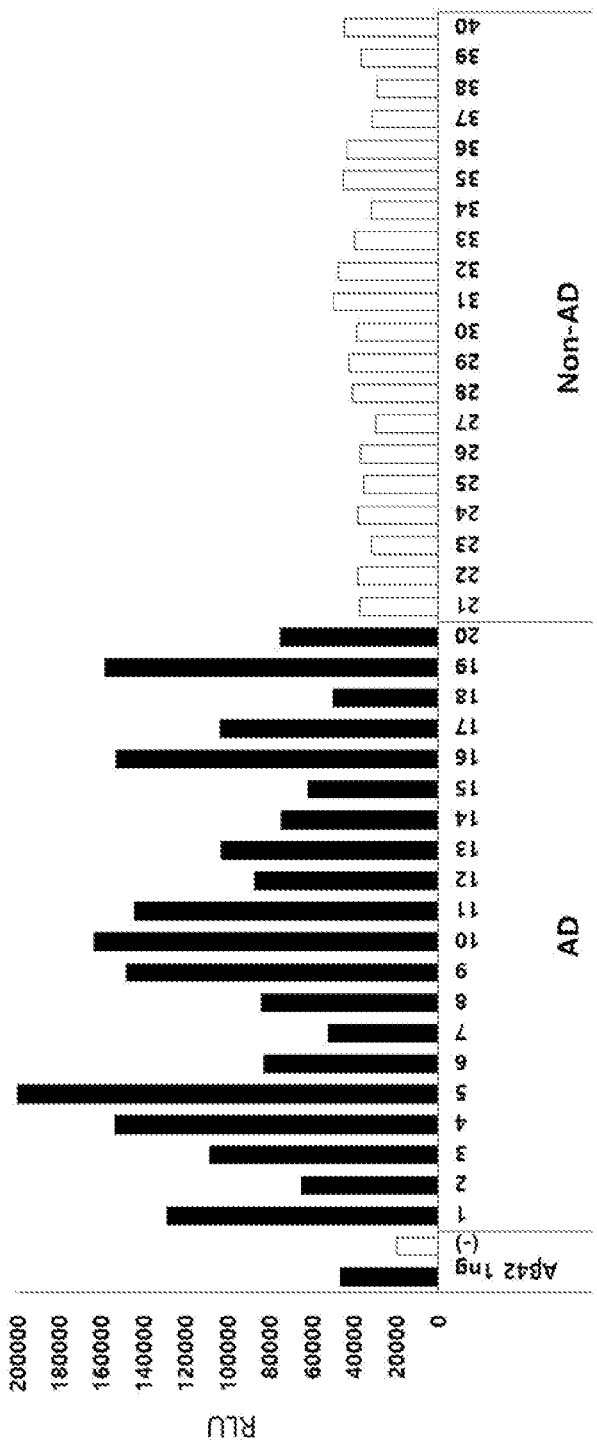

FIGS. 1 and 2 show signal changes in AD samples and Non AD samples according to the incubation time after the addition of S26C-Beta-Amyloid (1-40) Dimer. A difference between AD and Non AD is shown in each condition of incubation for 3 and 4 days.

It is determined from FIGS. 1 and 2 that the reason why signals of the Aβ oligomer were higher in the AD patient samples compared with the Non AD patient samples is that the clearing system suppressing the formation of Aβ oligomer in the AD patient samples was less activated than that in the Non AD patient samples.

Example 7

6E10/FF51HRP Set

Detection of Aβ oligomer using multimer detection system (MDS) from samples incubated for 0 and 4 days after treatment with S26C-Beta-Amyloid (1-40) Dimer The positive control, the negative control, and the samples treated with 0.25 g of S26C-Beta-Amyloid (1-40) Dimer and incubated for 0, 1, 2, 3, 4, and 5 days were dispensed in 100 μl each on 6E10 coated plate (3 μg/ml), followed by reaction at room temperature for 1 hour. The plate was washed three times with TBST. FF51-HRP antibody was added to buffer A to reach 0.5 μg/ml, and then 100 μl each was dispensed. The plate was washed three times with TBST, and 100 μl of the ECL solution was dispensed. The plate reacted with ELC was inserted into a luminometer (PerkinElmer) to measure a luminescent signal. Results are shown in FIG. 3.

Figure 3:
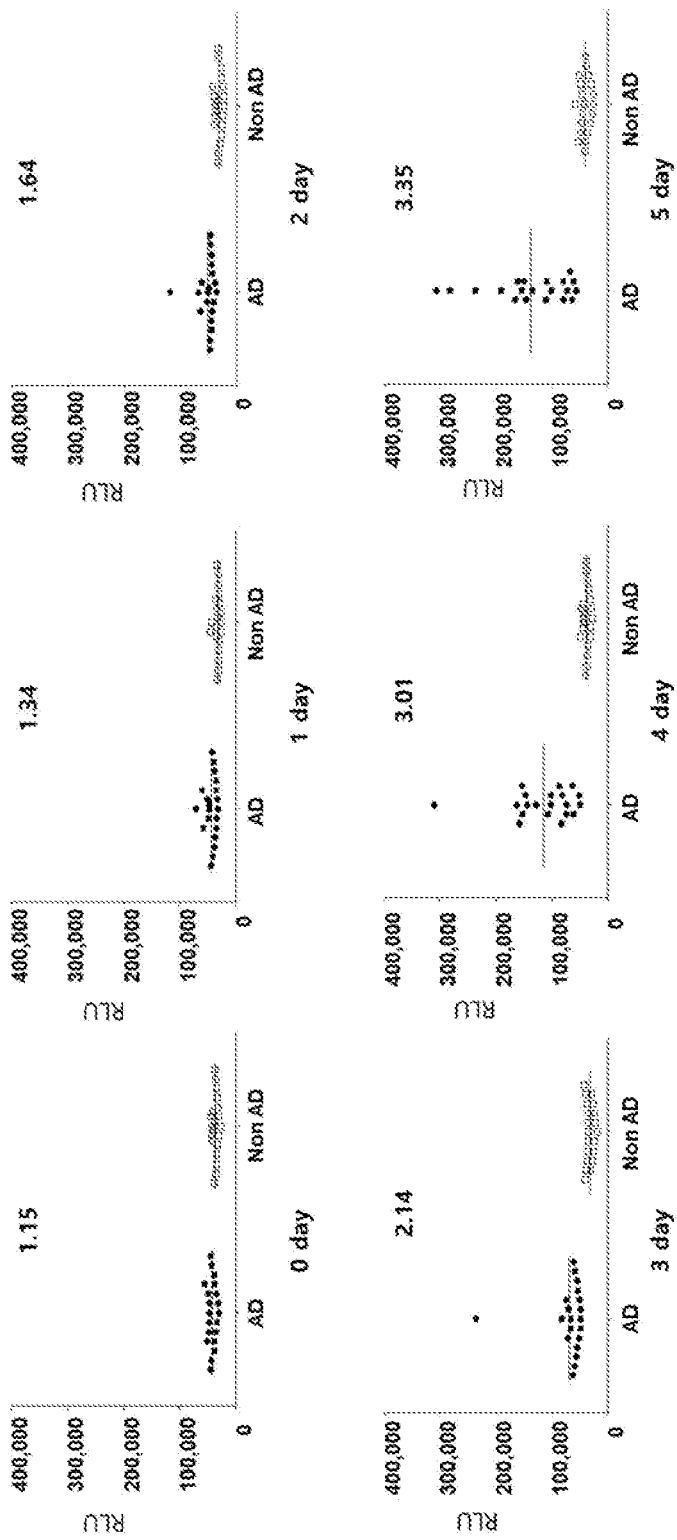
FIG. 3 shows the detection results of Aβ oligomer using multimer detection system (MDS) (6E10/FF51HRP set) from samples incubated for 0, 1, 2, 3, 4, and 5 days after treatment with S26C-Beta-Amyloid (1-40) Dimer according to an example of the present invention.

FIG. 3 shows a graph confirming signal changes in AD samples and Non AD samples according to the incubation time after the addition of S26C-Beta-Amyloid (1-40) Dimer. FIG. 3 shows that the signals of the AD samples were increased by 1.15 times, 1.34 times, 1.64 times, 2.14 times, 3.01 times, and 3.35 times compared with the signals of the Non AD samples.

It is determined from FIG. 3 that the reason why the signals of the Aβ oligomer were higher in the AD patient samples compared with the Non AD patient samples is that the clearing system suppressing the formation of the Aβ oligomer in the AD patient samples was less activated than that in the Non AD patient samples.

Example 8

6E10/FF51HRP Set

Detection of Aβ oligomer using multimer detection system (MDS) from samples incubated for 0 and 5 days after treatment with and without S26C-Beta-Amyloid (1-40) Dimer The positive control, the negative control, the samples treated with or without 0.25 ng of S26C-Beta-Amyloid (1-40) Dimer and incubated for 0 and 5 days were dispensed in 100 µl each on 6E10 coated plate (0 µg/ml), followed by reaction at room temperature for 1 hour. The plate was washed three times with TBST. FF51-HRP antibody was added to buffer A to reach 0.5 µg/ml, and then 100 µl each was dispensed. The plate was washed three times with TBST, and 100 µl of the ECL solution was dispensed. The plate reacted with ELC was inserted into a luminometer (PerkinElmer) to measure a luminescent signal. Results are shown in FIG. 4.

Figure 4:
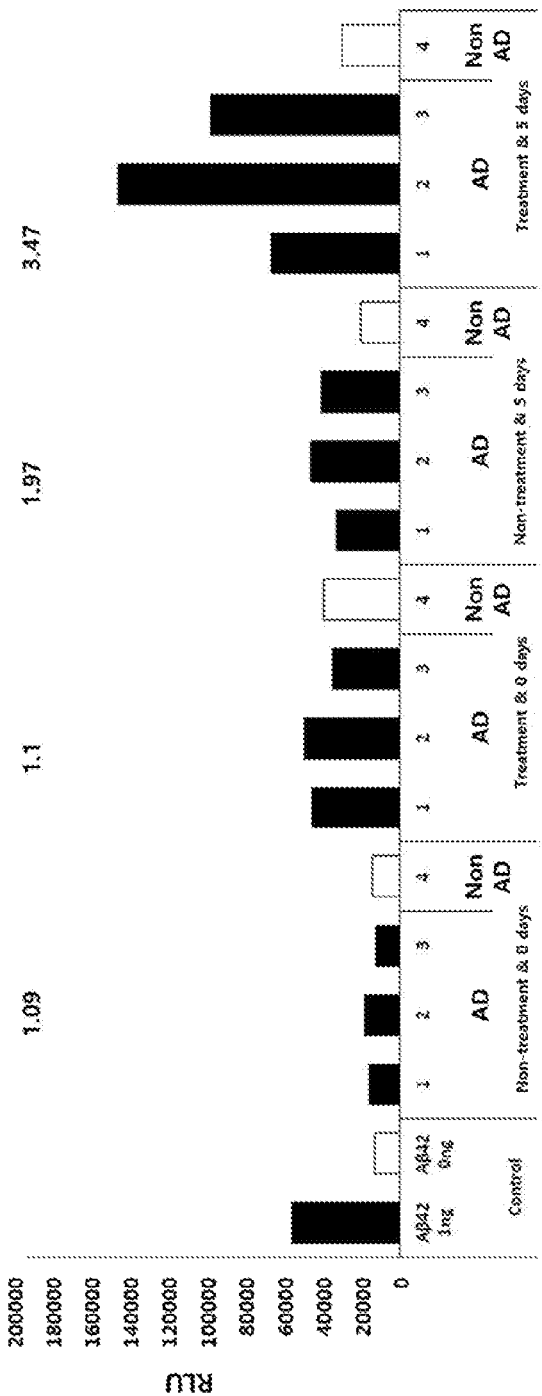
FIG. 4 shows the detection results of Aβ oligomer using multimer detection system (MDS) (6E10/FF51HRP set) from samples incubated for 0 and 5 days after treatment with or without 0.25 ng of S26C-Beta-Amyloid (1-40) Dimer according to an example of the present invention.

FIG. 4 shows the Aβ oligomer measurement data in the samples without or with the addition of S26C-Beta-Amyloid (1-40) Dimer and then incubated for 0 and 5 days. FIG. 4 shows that the signals of the AD samples were increased compared with the signals of the Non AD samples according to the time the absence and presence of spiking with Beta-Amyloid (1-40) Dimer.

The samples spiked without S26C-Beta-Amyloid (1-40) Dimer and incubated for 0 and 5 days showed 1.09-fold and 1.97-fold differences in the AD signals compared with the Non AD signals, respectively, and the variation of Aβ oligomer was a 1.8-fold increase from day 0 to day 5. Whereas, the samples spiked with S26C-Beta-Amyloid (1-40) Dimer and incubated for 0 and 5 days showed 1.1-fold and 3.47-fold differences in the AD signals compared with the Non AD signals, respectively, and the variation of Aβ oligomer was a 3.15-fold increase from day 0 to day 5.

It is determined from FIG. 4 that the reason why the signals of the Aβ oligomer were higher in the AD patient samples compared with the Non AD patient samples is that the clearing system suppressing the formation of the Aβ oligomer in the AD patient samples was less activated than that in the Non AD patient samples.

Example 9

6E10/WO2HRP Set

Detection of Aβ oligomer using multimer detection system (MDS) from samples incubated for 1 and 2 days after treatment with S26C-Beta-Amyloid (1-40) Dimer The positive control, the negative control, and the samples treated with 0.25 ng of S26C-Beta-Amyloid (1-40) Dimer and incubated for 1 and 2 days were dispensed in 100 µl each on 6E10 coated plate (3 µg/ml), followed by reaction at room temperature for 1 hour. The plate was washed three times with TBST. WO2-HRP antibody was added to buffer A to reach 0.25 µg/ml, and then 100 µl each was dispensed. The plate was washed three times with TBST, and 100 µl of the ECL solution was dispensed. The plate reacted with ELC was inserted into a luminometer (PerkinElmer) to measure a luminescent signal. The results are shown in FIGS. 5 and 6.

Figure 5:
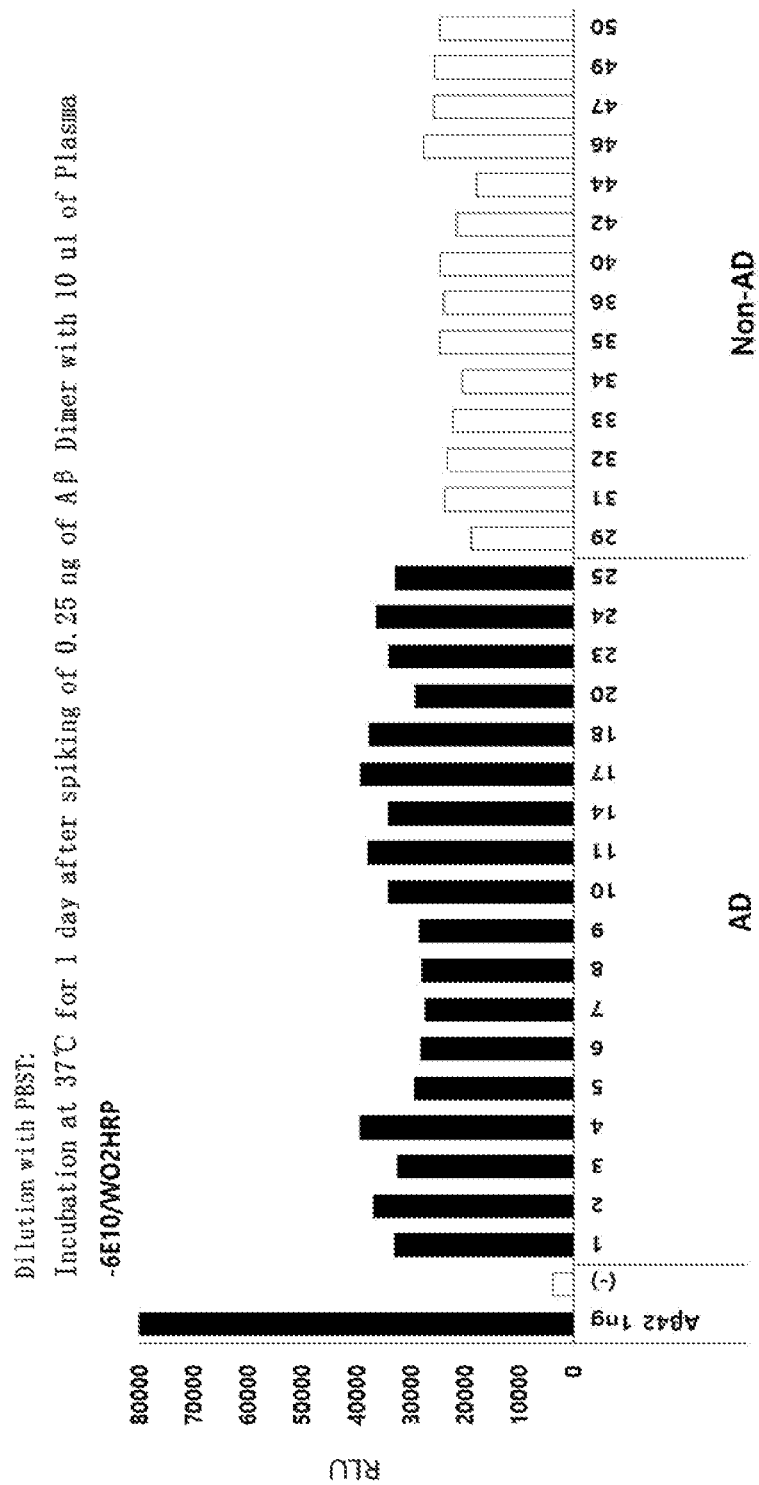
FIGS. 5 and 6 show the detection results of Aβ oligomer using multimer detection system (MDS) (6E10/WO2HRP set) from samples incubated for 1 and 2 days after treatment with S26C-Beta-Amyloid (1-40) Dimer according to examples of the present invention.
Figure 6:
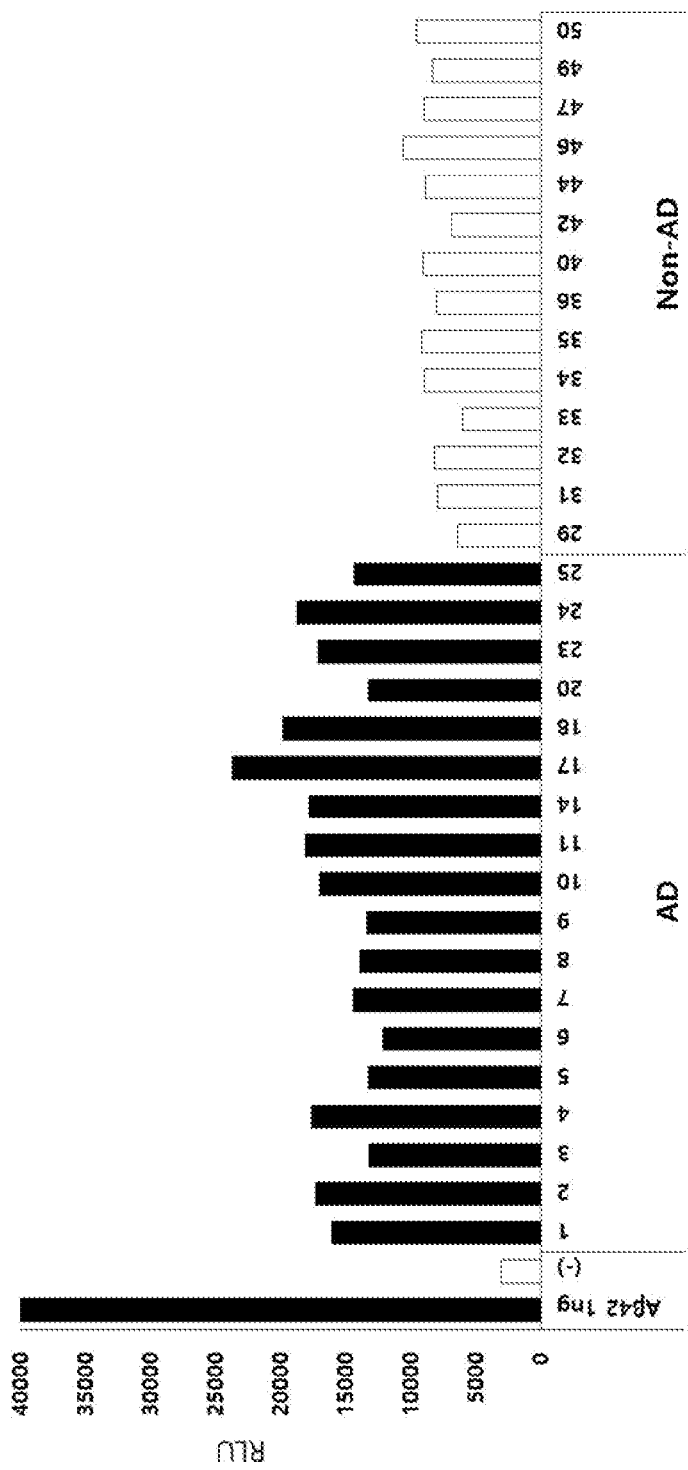

FIGS. 5 and 6 show signal changes in AD samples and Non AD samples according to the incubation time after the addition of S26C-Beta-Amyloid (4-40) Dimer. A difference between AD and Non AD is shown in each condition of incubation for 1 and 2 days.

Considering FIGS. 5 and 6, the reason why signals of the Aβ oligomer were higher in the AD patient samples compared with the Non AD patient samples is considered to be that the clearing system suppressing the formation of Aβ oligomer in the AD patient samples was less activated than that in the Non AD patient samples.

Example 10

6E10/WO2HRP Set

Detection of Aβ oligomer using multimer detection system (MDS) from samples incubated for 1 and 2 days after treatment with S26C-Beta-Amyloid (1-40) Dimer The positive control, the negative control, and the samples treated with 0.25 ng of S26C-Beta-Amyloid (1-40) Dimer and incubated for 3 and 4 days were dispensed in 100 µl each on 6E10 coated plate (3 µg/ml), followed by reaction at room temperature for 1 hour. The plate was washed three times with TBST. WO2-HRP antibody was added to buffer A to reach 0.25 µg/ml, and then 100 µl each was dispensed. The plate was washed three times with TBST, and 100 µl of the ECL solution was dispensed. The plate reacted with ELC was inserted into a luminometer (PerkinElmer) to measure a luminescent signal. Results are shown in FIG. 7.

Figure 7:
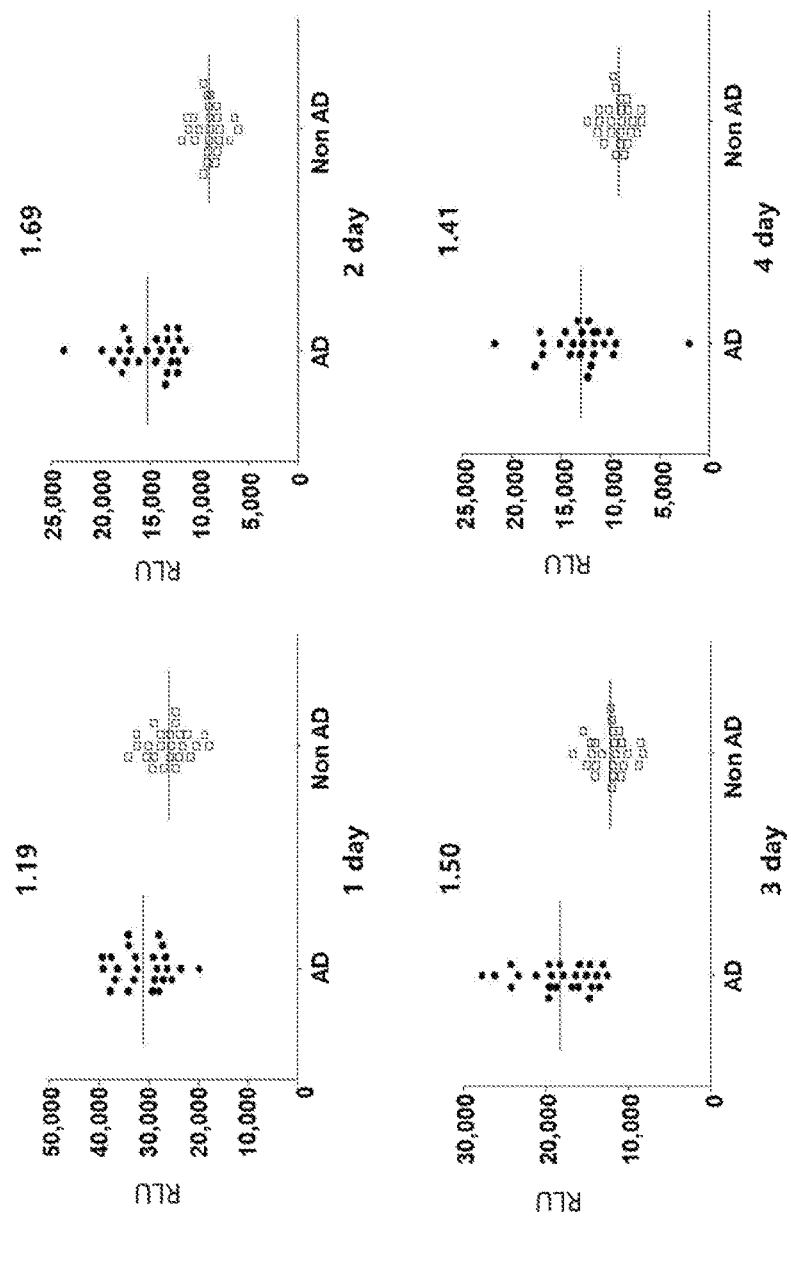
FIG. 7 shows the detection results of Aβ oligomer using multimer detection system (MDS) (6E10/WO2HRP set) from samples incubated for 1, 2, 3, and 4 days after treatment with S26C-Beta-Amyloid (1-40) Dimer according to an example of the present invention.

FIG. 7 shows a graph confirming signal changes in AD samples and Non AD samples according to the incubation time after the addition of S26C-Beta-Amyloid (5-40) Dimer. As a result, on day 1 of incubation, the average signal of AD samples was 1.19-fold greater than that of Non AD samples, and the sample signals were increased overall. Whereas, on days 2, 3, and 4, the sample signal values, which have been high overall, was dropped and thus the AD samples showed 1.69-fold, 1.50-fold, and 1.41-fold differences compared with the Non AD samples.

It is determined from FIG. 7 that the reason why the signals of the Aβ oligomer were higher in the AD patient samples compared with the Non AD patient samples is that the clearing system suppressing the formation of the Aβ oligomer in the AD patient samples was less activated than that in the Non AD patient samples.

This application contains references to amino acid sequences and/or nucleic acid sequences which have been submitted herewith as the sequence listing text file. The aforementioned sequence listing is hereby incorporated by reference in its entirety pursuant to 37 C.F.R. § 1.52(e).

What is claimed is:

1. A method for detecting an aggregate form of an Aβ peptide in a biosample from a subject, the method comprising the steps of:
    (a) spiking a biosample with a purified dimeric form of the Aβ peptide;
    (b) forming an aggregate form of the Aβ peptide by incubating a product of step (a);
    (c) contacting, with a product of step (b), a binder-label in which a signal generating label is conjugated to a binder binding to the aggregate form of the aggregate-forming polypeptide; and
    (d) detecting a signal generated from the binder-label bound to the aggregate form of the aggregate-forming polypeptide,
        wherein the subject is suffering from Alzheimer's disease or suspected of suffering from Alzheimer's disease,
        wherein the incubating in step (b) is carried out for a sufficient time for multimerization of the spiked dimeric form of the Aβ peptide,
        wherein steps (c) and (d) are performed by comprising the following steps:
            (c-1) contacting the product of step (b) with a capture antibody recognizing an epitope on the Aβ peptide capturing the aggregate form;
            (c-2) contacting the captured aggregate form with the binder-label recognizing an epitope on the Aβ peptide, wherein the binder is selected from the group consisting of an antibody, a peptide aptamer, an adnectin, an affibody, an avimer, and a Kunitz domain; and
            (c-3) detecting an aggregate form-detection antibody complex.

2. The method of claim 1, wherein the incubation time is a time sufficient to enhance a signal generated using the biosample to be 1.3-20 times greater than a signal generated using a biosample from a normal human being.

3. The method of claim 1, wherein the biosample is blood.

4. The method of claim 3, wherein the blood sample is plasma.

5. The method of claim 1, wherein the dimeric form of the Aβ peptide is a dimeric form formed by disulfide bonding of the 26th Cys residues of the Aβ peptides each comprising the amino acid sequences of SEQ ID NO: 1.

6. The method of claim 1, wherein a buffer is additionally added to the product of step (a).

7. The method of claim 6, wherein the buffer is added in an amount of 3-15 times (v/v) relative to an amount of the biosample.

8. The method of claim 7, wherein the buffer is a non-ionic surfactant-containing phosphate buffer.

9. The method of claim 1, wherein the forming of the aggregate form of the AB peptide in step (b) is carried out by incubating the product of step (a) at a temperature of 1-50° C.

10. The method of claim 1, wherein the detection antibody is a detection antibody recognizing an epitope identical to or overlapped with the epitope in step (c-1).

11. The method of claim 1, wherein the capture antibody is bound to a solid substrate.

12. The method of claim 1, wherein the binder-label is a detection antibody conjugated to a label generating a detectable signal.

13. The method of claim 12, wherein the label bound to the detection antibody includes a compound label, an enzyme label, a radioactive label, a fluorescent label, a luminescent label, a chemiluminescent label, and a FRET label.

* * * * *

SEQUENCE LISTING

```
<160> NUMBER OF SEQ ID NOS: 1

<210> SEQ ID NO 1
<211> LENGTH: 40
<212> TYPE: PRT
<213> ORGANISM: Homo sapiens

<400> SEQUENCE: 1

Asp Ala Glu Phe Arg His Asp Ser Gly Tyr Glu Val His His Gln Lys
1               5                   10                  15
```

```
Leu Val Phe Phe Ala Glu Asp Val Gly Cys Asn Lys Gly Ala Ile Ile
            20                  25                  30
Gly Leu Met Val Gly Gly Val Val
            35              40
```